US010933195B1

(12) United States Patent
Lytvyn et al.

(10) Patent No.: US 10,933,195 B1
(45) Date of Patent: *Mar. 2, 2021

(54) SYRINGE HAVING A MECHANICALLY OPERATED MECHANISM FOR INJECTING PRECISE VOLUMES OF A SOLUTION

(71) Applicants: Andriy Lytvyn, Tampa, FL (US); Irina M. Lytvyn, Tampa, FL (US)

(72) Inventors: Andriy Lytvyn, Tampa, FL (US); Irina M. Lytvyn, Tampa, FL (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/252,950

(22) Filed: Jan. 21, 2019

Related U.S. Application Data

(63) Continuation of application No. 15/186,427, filed on Jun. 18, 2016, now Pat. No. 10,213,555.

(51) Int. Cl.
*A61M 5/315* (2006.01)

(52) U.S. Cl.
CPC .... *A61M 5/31515* (2013.01); *A61M 5/31585* (2013.01); *A61M 5/31556* (2013.01); *A61M 2005/3152* (2013.01)

(58) Field of Classification Search
CPC ...... A61M 2005/3152; A61M 5/31578; A61M 5/31576; A61M 5/31583; A61M 5/31585; A61M 5/31558; A61M 5/31575; A61M 5/31581

See application file for complete search history.

(56) References Cited

U.S. PATENT DOCUMENTS 2,725,877 A * 12/1955 Reiter ................. A61M 5/20
604/135

* cited by examiner

*Primary Examiner* — Emily L Schmidt
(74) *Attorney, Agent, or Firm* — Andriy Lytvyn

(57) ABSTRACT

A syringe having a mechanical ejection mechanism. The ejection mechanism includes an actuator and a rotational gear. The actuator has a retractable pawl configured to engage the gear when the actuator is displaced from a non-depressed position into a depressed position. Displacement of the actuator causes the gear to rotate by a predetermined angle. The rotation of the gear is translated into linear displacement of the plunger within the barrel, thereby ejecting a predetermined amount of solution from the barrel.

10 Claims, 4 Drawing Sheets

SYRINGE HAVING A MECHANICALLY OPERATED MECHANISM FOR INJECTING PRECISE VOLUMES OF A SOLUTION

PRIORITY CLAIM

This application claims priority to a co-pending U.S. non-provisional application entitled "SYRINGE HAVING A MECHANICALLY OPERATED MECHANISM FOR INJECTING PRECISE VOLUMES OF A SOLUTION" having a Ser. No. 15/186,427 filed on Jun. 18, 2016.

BACKGROUND OF THE INVENTION

1. Field of the Invention

This invention relates to medical syringes. More specifically, it relates to a syringe with a mechanically-operated mechanism for injecting a precise volume of a liquid.

2. Brief Description of the Related Art

The hypodermic needle for subcutaneous injections was invented by Francis Rynd in 1844. Since then, hypodermic syringes have become ubiquitous in modern medicine. However, despite the immense advancements in medicine, the basic structure of the most commonly used syringes has remained unchanged for several decades. Most medical syringes comprise a single moving part—the plunger—that is moved manually by a skilled practitioner. The reason for this simplicity is the precision with which the dosages of medication must be delivered into patient's body. The medical syringes permit no margin of error and, therefore, they must be designed with as few structural complexities as possible. Moreover, because medical syringes come in contact with medications and bodily fluids, most syringes are disposed of immediately after a single use. For this reason, a medical office or a hospital can use several thousand syringes a single day. Therefore, the cost of the medical syringes must be kept as low as possible, which further imposes limitations on practicability of their design.

In most applications, the medical practitioner draws the precise amount of medicine into the syringe and then injects the entirety of the drawn volume into a patient through a single injection. However, in some applications, such as injection of botulinum toxin, requires multiple injections into multiple sites. The common procedure is to drawn a total volume of the liquid into the barrel of the syringe and then, using the demarcation lines for guidance injecting the required amount into each site. This practice results in imprecise volumes being injected for several reasons.

First, the demarcation lines are closely positioned with respect to one another and visually aligning the distal end of the plunger with the correct demarcation line is quite difficult especially considering that the practitioner is usually reading the demarcation lines at an angle. Second, to ensure displacement of a precise amount of liquid the plunger must move in very small increments. In practice, this is quite difficult because when a practitioner applies an amount of force sufficient to overcome the static friction between the seal of the plunger and the interior surface of the barrel, the practitioner cannot immediately reduce the force once the plunger starts moving and the coefficient of friction reduces. The reaction time, steadiness of the hand, and reflexes of the practitioner impose limits on the minimum increment at which the practitioner can move the plunger. This limitation restricts the precision of volume of the injected liquid. In applications requiring multiple injections, these imprecisions can compound with each injection. One imperfect way to reduce potential damage due to the imprecise injections is to lower the concentration of the solution being injected. This practice, however, also has some significant drawbacks associated with larger amounts of liquid being injected into each site. Finally, conventional medical syringes are uncomfortable for botulin toxin injections. The medical provider must simultaneously hold the patient's skin and the syringe (often an uncomfortable angle) with one hand, while ensuring that the fingers do not obstruct the visibility of the demarcation lines, and pushing the plunger with the other hand until the distal end of the plunger aligns with a predetermined demarcation line.

A variety of hypodermic needles capable of dispensing precise amounts of solution are known in the art and are commonly referred to as insulin pens. Insulin pens, however, are generally fairly complex and are significantly more expensive than disposable syringes. For diabetics, the cost of insulin pens is offset by their reusability—a patient can use a single pen for a prolonged period of time because this type of syringe only delivers a single type of solution and is only used by a single patient. However, for single-use applications, such botulin toxin injections, the high cost of the insulin pens makes them impractical.

Accordingly, what is needed, is a disposable low-cost hypodermic syringe with a mechanical injection mechanism that precisely controls the amount of liquid being ejected from the syringe into a site. Preferably, the injection actuator is positioned on a side of a barrel to facilitate the comfort of use.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
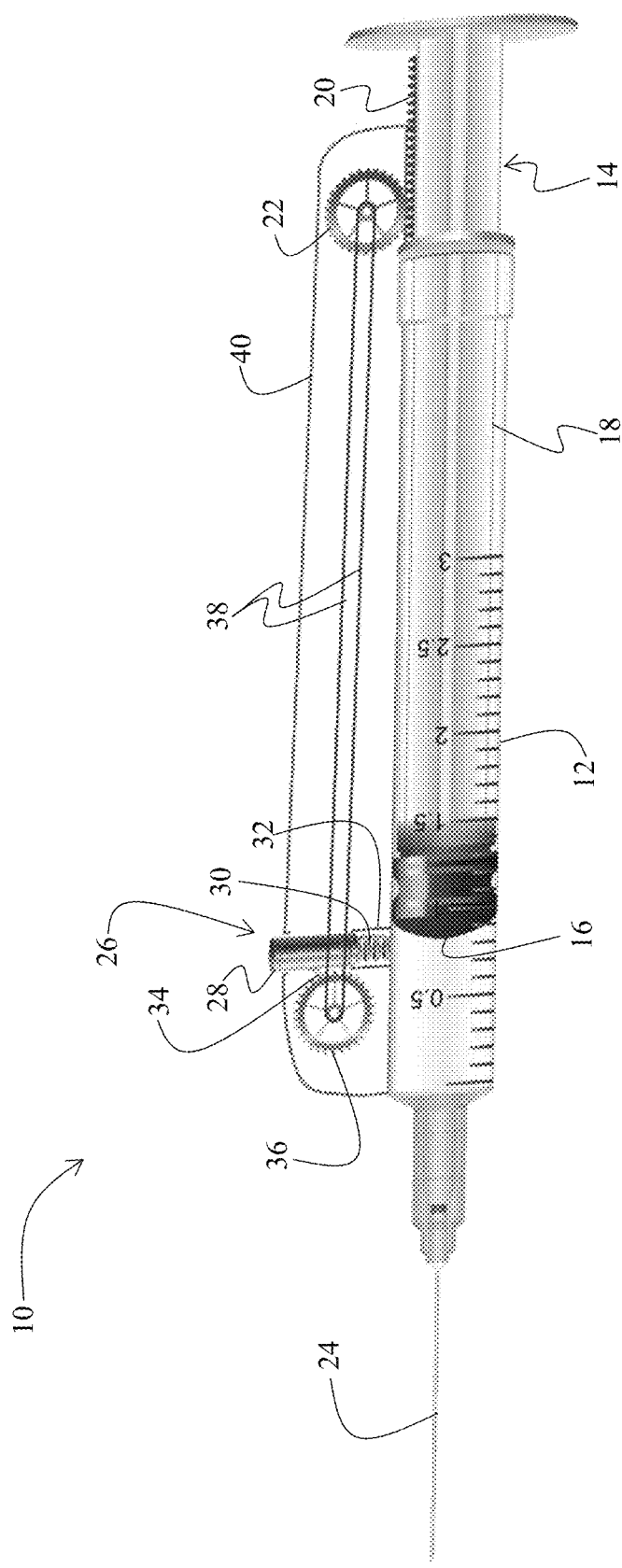
FIG. 1 is a cross-sectional side view of a first embodiment of the invention.

FIG. 1 depicts the hypodermic syringe 10 according to an embodiment of the invention. Hypodermic syringe 10 includes a cylindrical barrel 12 configured to house a liquid solution. A plunger 14 is slidingly disposed within barrel 12. The outer circumference of distal end 16 of plunger 14 mates with the inner circumference of barrel 12, whereby distal end 16 of plunger 14 forms a fluid impermeable seal with the interior surface of barrel 12. A rubber seal may be disposed at distal end 16 to ensure a hermetic seal between distal end 16 and inner surface of barrel 12. Plunger 14 has a substantially rigid elongated body 18. At least one side of plunger 14 includes a plurality of gear teeth forming a rack gear 20. The gear teeth all have the same size and are equidistantly spaced from one another.

FIG. 1 further depicts a pinion gear 22 rotationally disposed at a proximal end of barrel 12. Pinion gear 22 engages rack gear 20, thereby forming a rack-gear assembly. The rotational motion of pinion gear 22 causes rack gear 20 to move linearly along a center axis of barrel 12, which movement pushes plunger 14 into barrel 12. Displacement of distal end 16 of plunger 14 expels solution contained within barrel 12 through lumen of needle 24. Needle 24 is in fluid communication with barrel 12.

FIG. 1 further depicts a mechanically-actuated ejection mechanism 26 positioned on the outer surface of barrel 12. Ejection mechanism 26 includes a mechanical actuator 28. In one embodiment, the mechanical actuator 28 is a push button having a depressed and non-depressed positions. Actuator 28 is biased toward a non-depressed position by a biasing element 30. Biasing element 30 may be a helical compression spring, a piece of rubber or another polymer, a magnet, or any other biasing means known in the art. The displacement distance of actuator 28 is limited by sheath 32 in which actuator 28 resides. Therefore, the maximum distance actuator 28 is capable of moving remains constant and is unaffected by the magnitude of the force applied onto actuator 28.

Figure 2B:
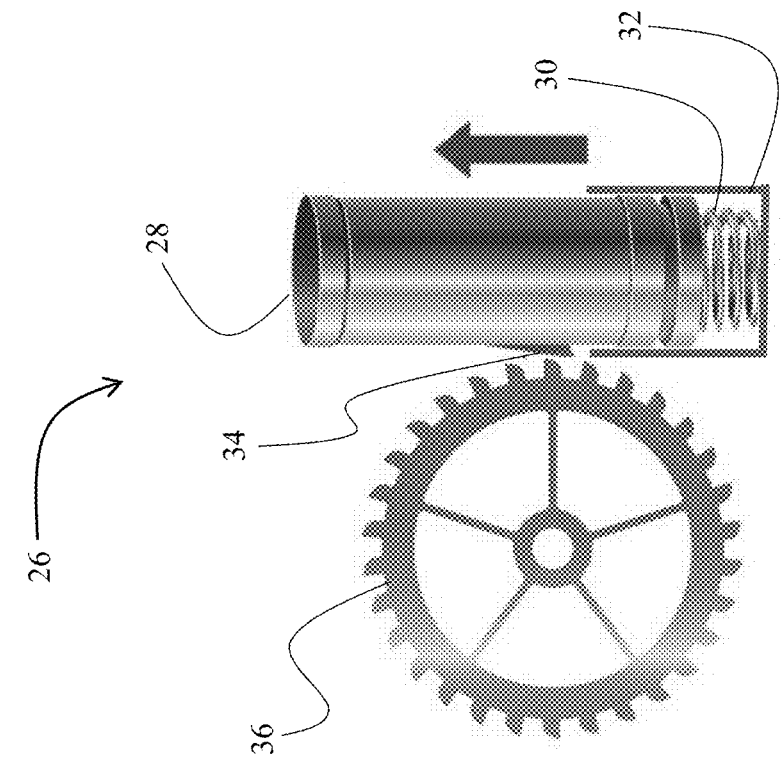
FIG. 2B is a schematic view depicting the retracted position of the retractable pawl as the biasing element returns the actuator to its initial position.
Figure 2A:
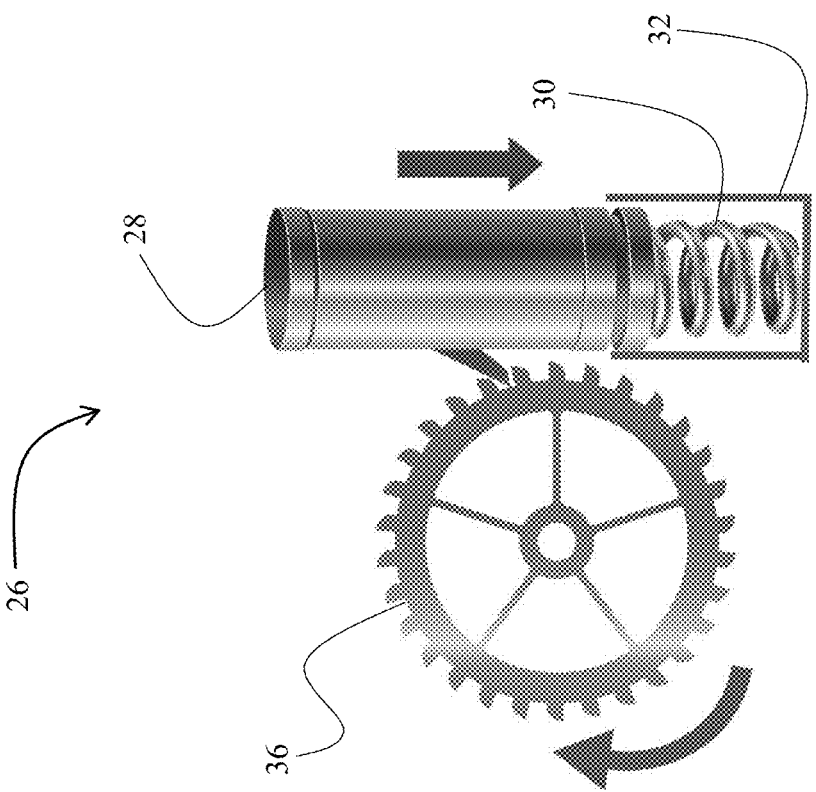
FIG. 2A is a schematic view depicting the extended position of the retractable pawl as the actuator is being displaced.

As shown in FIG. 2A, ejection mechanism 26 contains a pawl 34 protruding through a lateral surface of actuator 28. A ratchet gear 36 is rotationally disposed in a proximity to actuator 28. Pawl 34 of actuator 28 engages the teeth of ratchet gear 36 as actuator 28 transitions from a first non-depressed position to a second depressed position. When a sufficient force is applied onto actuator 28, actuator 28 is linearly displaced from the non-depressed position into the depressed position. During the displacement of actuator 28 from the non-depressed position into the depressed position, pawl 34 engages the teeth of ratchet gear 36 causing ratchet gear 36 to rotate.

As illustrated in FIG. 2B, after the force applied onto actuator 28 is removed, biasing element 30 returns actuator 28 back to its initial non-depressed position. During the transition of actuator 28 from the depressed position to the non-depressed position, pawl 34 retracts away from ratchet gear 36, thereby resulting in no counter-rotation of ratchet gear 36 which remains stationary. When actuator 28 is in its initial non-depressed position, pawl 34 does not engage ratchet gear 36, thereby allowing ratchet gear 36 to rotate independently of actuator 28. This feature allows the user to manually retract plunger 14 as the user would with any standard syringe. The user can also eject the solution from the syringe by manually pushing plunger 14 without requiring the use of the actuation mechanism. Therefore, the user can use syringe 10 as the user would use any standard syringe, but, unlike a standard syringe, the user has an option of using ejection mechanism 26 to eject precise amounts of solution.

Figure 3:
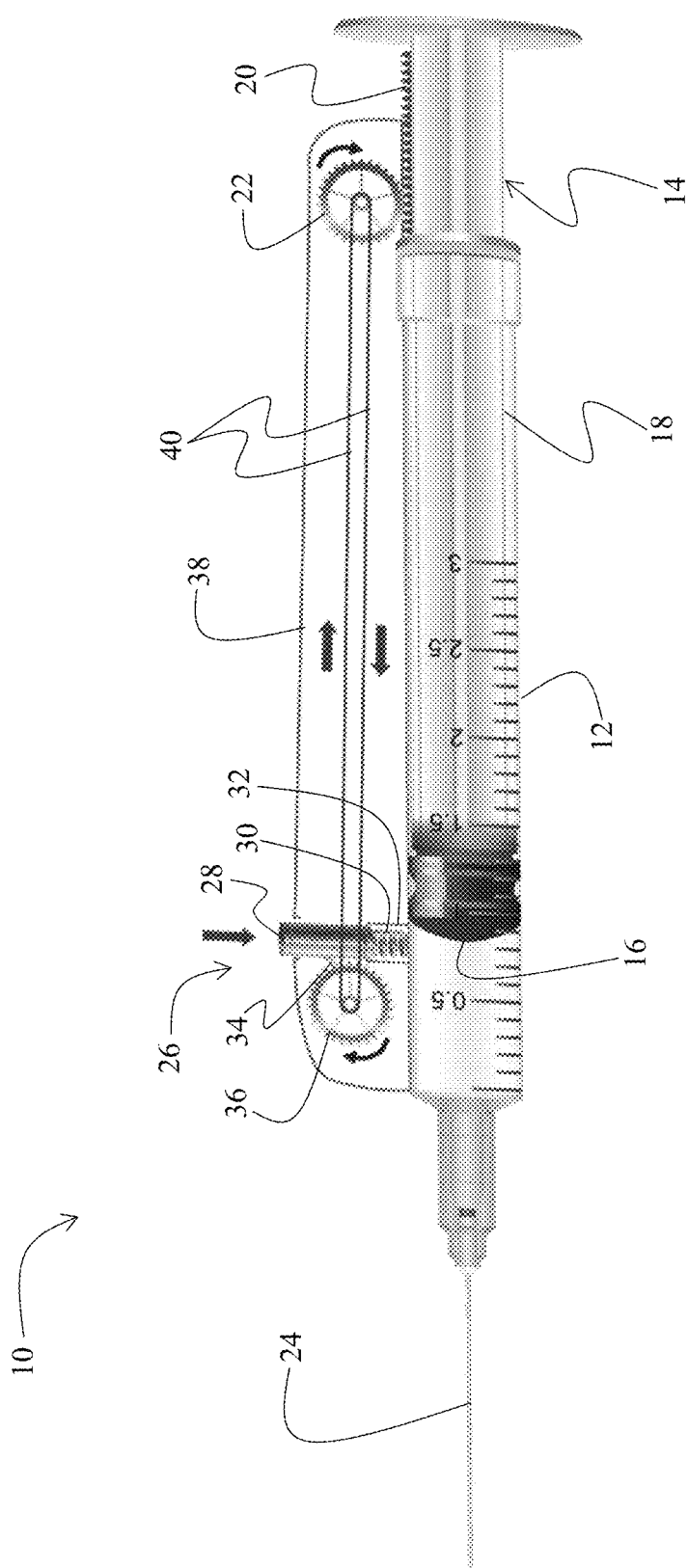
FIG. 3 is a schematic cross-sectional view depicting rotation and movement of components of the invention responsive to a force being applied onto the actuator.

FIG. 3 further depicts a belt 38 connecting ratchet gear 36 and a pinion gear 22. Pulleys may be disposed within pinion gear 22 and ratchet gear 36, whereby belt 38 engages both pulleys. Belt 38 translates the rotational motion of ratchet gear 36 to pinion gear 22. When actuator 28 transitions from the initial non-depressed position into a depressed position, pawl 34 engages the teeth of ratchet gear 36 causing it to rotate. Belt 38 translates the rotation of ratchet gear 36 to pinion gear 22 causing pinion gear 22 to rotate also. Pinion gear 22 translates its rotational motion into the linear motion of rack gear 20 disposed along plunger 14, thereby causing distal end 16 of plunger 14 to move along a center axis of barrel 12. Distal end 16 of plunger 14 sealingly engages the inner surface of barrel 12, and, therefore, the linear motion of barrel 12 increases the pressure within barrel 12, thereby ejecting a volume of solution from barrel 12 through the needle attached to distal end 16 thereof.

As disclosed above, the maximum downward displacement of actuator 28 is limited by sheath 32 in which actuator 28 resides. Accordingly, the maximum rotation of ratchet gear 36, pinion gear 22 and, displacement of plunger 14 per each full displacement of actuator 28 remain constant. The radii of the pulleys within pinion gear 22 and ratchet gear 36 and the spacing of the gear teeth are configured to displace plunger 14 by a predefined distance every time actuator 28 is transitioned from its initial non-depressed position into the depressed position. A person of ordinary skill in art understands the mathematical principles according to which the gear ratios and the size of the gear teeth can be readily calculated so that a single full displacement of actuator 28 displaces plunger 14 by a known predefined distance.

The force applied onto actuator 28 must exceed the biasing force of biasing element 30 and the total static friction forces between all moving components of syringe and ejection mechanism 26. For example, the static friction forces exist between the seal of plunger 14 and the interior surface of barrel 12, the friction between the gears and belt 38, the friction between the gears and the axels about which they rotate, and the friction between actuator 28 and sheath 32. If the force applied to actuator 28 exceeds the total friction force and the biasing force of biasing element 30, actuator 28 will be displaced causing plunger 14 to move by a predefined distance. Once the force applied onto actuator 28 is removed, the biasing force of biasing element 30 must be sufficient to cause pawl 34 to retract away from ratchet gear 36 to bring actuator 28 into its initial position. During this movement, the force required to retract pawl 34 must not exceed the frictional forces within ejection mechanism 26, thereby ensuring that plunger 14 remains stationary while actuator 28 returns to its original position.

In an embodiment, the displacement distance of plunger 14 corresponds to ejection of a single unit of botulinum toxin from barrel 12. The correlation between the displacement of plunger 14 and the amount of solution ejected from the syringe can be readily calculated based on the inner diameter of barrel 12 and the concentration of the solution. The dimensions of all components involved in the mechanical ejection mechanism 26 described herein can be selected based on the amount of solution that is desired to be ejected with each full displacement of actuator 28.

FIG. 1 further depicts that the components of ejection mechanism 26 can be enclosed by a case 40 to improve ergonomic characteristics and aesthetic appearance of syringe 10. Case 40 exposes a portion of barrel 12, so that the user can visibly confirm the presence of the solution within barrel 12 and its volume. The demarcation lines remain of barrel 12 are visible, thus allowing the user to visually verify the amount of solution being ejected.

To operate syringe 10, a user draws a solution into barrel 12 by manually pulling back plunger 14 as he or she would do with a standard syringe. This causes pinion gear 22 and thereby ratchet gear 36 to rotate. Since actuator 28 is in its default position, pawl 34 of actuator 28 does not engage the teeth of ratchet gear 36, and therefore, the rotation of ratchet gear 36 caused by barrel 12 being pulled back does not affect actuator 28. In an alternative embodiment, pinion gear 22 may be configured to disengage rack gear 20 when the user is pulling back plunger 14 or manually pushing plunger 14 this. In this embodiment, the user can manually operate syringe 10 as he or she would operate a conventional syringe.

Once the appropriate amount of solution is drawn into barrel 12, the practitioner is able to hold the syringe in one hand placing a finger onto actuator 28. This frees up the other hand to hold the patient's skin to increase the precision of the injection and decrease the discomfort to the patient. Once the needle is injected into the site, the practitioner presses down actuator 28 until actuator 28 cannot be displaced any further due to the constraints of sheath 32. The downward displacement of actuator 28 causes ratchet gear 36 to rotate. The rotational motion is translated to pinion gear 22 through belt 38. Rack gear 20 translates rotation of pinion gear 22 into linear movement of plunger 14, thus causing distal end 16 to eject solution from barrel 12. Accordingly, every time the practitioner fully displaces actuator 28 from the non-depressed position into the depressed position, plunger 14 moves by a predefined distance injecting the predefined amount of the solution into the patient. When the practitioner releases actuator 28, biasing element 30 causes actuator 28 to return to its initial non-depressed position without causing any further movement of plunger 14. The practitioner repeatedly presses and releases actuator 28 until the desired amount of the solution is injected into the site. Then, the practitioner removes the needle from the first site and injects subsequent sites using the same method.

Figure 4:
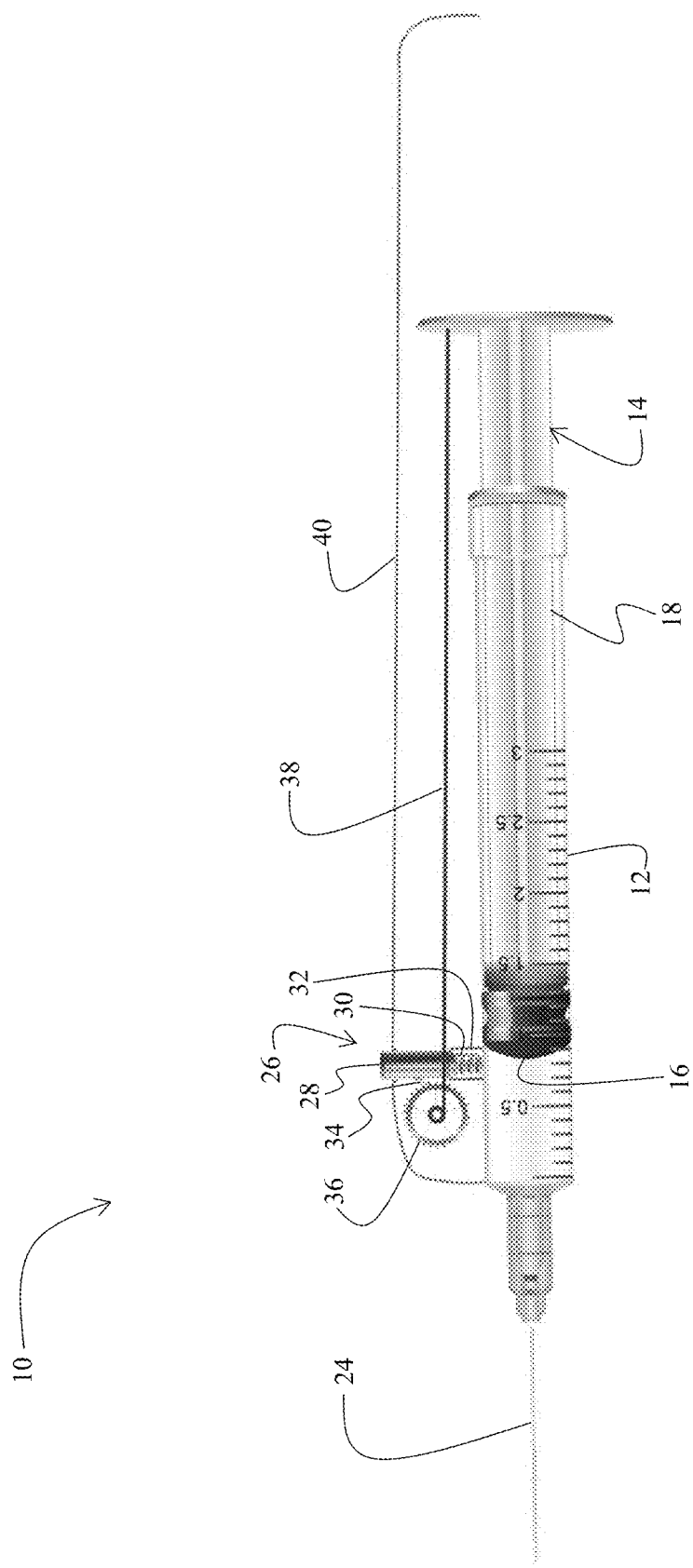
FIG. 4 is a cross-sectional side view of an alternative embodiment of the invention.

In another embodiment depicted in FIG. 4, pinion-rack gear assembly can be eliminated and one end of belt 38 may be directly attached to the proximal end of plunger 14. In this embodiment, the rotational motion of ratchet gear 36 would be transferred directly into a linear displacement of plunger 14. In alternative, a gear-pulley system can be used to translate the rotation of ratchet gear 36 into a linear displacement of plunger 14. A protective case may be used to enclose ejection mechanism 26 including the cable connected to plunger 14.

In an embodiment, plunger 14 may be biased toward a position in which plunger 14 is fully inserted into barrel 12. In this embodiment, a retention mechanism is used to restrict linear movement of plunger 14. An actuation mechanism causes the retention mechanism to temporarily release plunger 14. Biasing force exerted onto plunger 14 will push plunger 14 into barrel 12 until the retention mechanism reengages plunger 14 and immobilizes it against further movement. The retention mechanism is configured to permit plunger 14 to move by a predetermined distance with each actuation, thereby controlling the amount of solution ejected with each actuation.

It is further contemplated, that the ratchet mechanism may be replaced by another mechanism capable of causing a rotational motion of a gear-like component in response to the linear displacement of actuator 28. For example, distal end 16 of actuator 28 may contain a first ramp element. The top surface of the gear may contain a plurality of ramp elements, whose sloped surfaces contact the slopped surface of the first ramp element. The linear displacement of actuator 28 causes the first ramp element to slide along the second ramp element, thereby displacing the second ramp element and causing the gear to rotate. The rotation of the gear is translated into the linear displacement of plunger 14 as disclosed above. Biasing element 30 returns actuator 28 to its initial non-depressed position, while the subsequent ramp element of the gear engages a corresponding ramp element of actuator 28. Actuator 28 can be depressed again to eject the next incremental volume of the solution.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A syringe, comprising:
a barrel having an inner surface;
a plunger having an elongated body, a proximal end, and a distal end, the distal end being disposed within the barrel, wherein the distal end forms a fluid-impermeable seal with the inner surface of the barrel;
an ejection mechanism in a mechanical communication with the plunger, the ejection mechanism having an actuator, the actuator having a first initial position and a second displaced position, whereby responsive to displacement of the actuator from the first initial position to the second displaced position, the distal end of the plunger translates by a predetermined distance within the barrel;
wherein the plunger is configured to translate linearly within the barrel responsive to a force being applied onto the proximal end of the plunger, thereby enabling manual operation of the syringe while the actuator remains in the first initial position or the second displaced position, wherein a liquid can be drawn into the barrel of the syringe by manually retracting the plunger relative to the barrel.

2. A syringe according to claim 1, further comprising a biasing element urging the actuator toward the first initial position.

3. A syringe according to claim 1, further comprising a casing at least partially enclosing the ejection mechanism.

4. A syringe according to claim 1, the ejection mechanism comprising:
a first gear, wherein the actuator engages the first gear when the actuator transitions from the first initial position into the second displaced position causing the first gear to rotate by a predetermined angle of rotation;
wherein rotation of the first gear causes the distal end of the plunger to translate by the predetermined distance within the barrel.

5. A syringe according to claim 4, wherein, when the actuator is in the first initial position, the first gear can rotate without engaging the actuator.

6. A syringe according to claim 4, further comprising a pawl in mechanical communication with the actuator, the pawl having a first extended position and a second retracted position, wherein the pawl is configured to engage the first gear when the actuator is displaced from the first initial position into the second displaced position, thereby causing the first gear to rotate.

7. A syringe according to claim 4, wherein the first gear remains stationary during the actuator transitioning from the second displaced position into the first initial position.

8. A syringe according to claim 4, wherein the first gear is a ratchet gear.

9. A syringe according to claim 4, further comprising a cable connecting the first gear and the plunger.

10. A syringe according to claim 4, further comprising:
a second gear in mechanical communication with the first gear, wherein rotation of the first gear is translated to the second gear;
a plurality of gear teeth disposed along the elongated body of the plunger, the plurality of gear teeth engaging the second gear, collectively forming a rack-gear assembly, wherein rotation of the second gear is translated via the rack-gear assembly to the plunger thereby displacing the distal end of the plunger within the barrel.

* * * * *